(12) United States Patent
Koblish et al.

(10) Patent No.: US 8,795,271 B2
(45) Date of Patent: Aug. 5, 2014

(54) SURGICAL PROBE FOR SUPPORTING INFLATABLE THERAPEUTIC DEVICES IN CONTACT WITH TISSUE IN OR AROUND BODY ORIFICE AND WITHIN TUMORS

(75) Inventors: Josef V. Koblish, Palo Alto, CA (US); Anant V. Hegde, Newark, CA (US); David K. Swanson, Campbell, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1307 days.

(21) Appl. No.: 12/175,433

(22) Filed: Jul. 17, 2008

(65) Prior Publication Data
US 2009/0099564 A1 Apr. 16, 2009

Related U.S. Application Data

(63) Continuation of application No. 11/027,622, filed on Dec. 30, 2004, now abandoned, which is a continuation of application No. 09/737,176, filed on Dec. 13, 2000, now Pat. No. 6,837,885, which is a continuation-in-part of application No. 09/083,874, filed on May 22, 1998, now Pat. No. 6,428,537.

(51) Int. Cl.
*A61B 18/14* (2006.01)

(52) U.S. Cl.
USPC .................................. 606/41; 607/105

(58) Field of Classification Search
USPC .......... 606/27, 28, 41, 48–50; 607/101–105
See application file for complete search history.

(56) References Cited

U.S. PATENT DOCUMENTS

| | | |
|---|---|---|
| 4,565,200 A | 1/1986 | Cosman |
| 4,765,331 A | 8/1988 | Petruzzi |
| 4,784,133 A | 11/1988 | Mackin |
| 4,800,899 A | 1/1989 | Elliott |
| 5,007,908 A | 4/1991 | Rydell |
| 5,047,028 A | 9/1991 | Qian |
| 5,183,463 A | 2/1993 | Debbas |
| 5,207,672 A | 5/1993 | Roth et al. |
| 5,213,576 A | 5/1993 | Abiuso |
| 5,255,678 A | 10/1993 | Deslauriers et al. |
| 5,277,201 A | 1/1994 | Stern |
| 5,292,320 A | 3/1994 | Brown et al. |
| 5,329,923 A | 7/1994 | Lundquist |
| 5,368,591 A | 11/1994 | Lennox et al. |
| 5,380,319 A | 1/1995 | Saito |
| 5,403,311 A | 4/1995 | Abele |
| 5,409,483 A | 4/1995 | Campbell et al. |
| 5,431,649 A | 7/1995 | Mulier |
| 5,443,470 A | 8/1995 | Stern et al. |
| 5,472,441 A * | 12/1995 | Edwards et al. ............... 606/41 |
| 5,496,271 A | 3/1996 | Burton et al. |
| 5,496,311 A | 3/1996 | Abele et al. |

(Continued)

FOREIGN PATENT DOCUMENTS

| | | |
|---|---|---|
| DE | 2124684 A1 | 11/1972 |
| WO | WO-00/13602 A2 | 3/2000 |

(Continued)

*Primary Examiner* — Michael Peffley
(74) *Attorney, Agent, or Firm* — Seager, Tufte & Wickhem, LLC

(57) ABSTRACT

A probe that facilitates the creation of lesions in bodily tissue. The probe includes a relatively short shaft and an inflatable therapeutic element.

19 Claims, 7 Drawing Sheets

(56) References Cited

U.S. PATENT DOCUMENTS

| | | | |
|---|---|---|---|
| 5,505,730 A | 4/1996 | Edwards | |
| 5,569,241 A | 10/1996 | Edwards | |
| 5,624,392 A | 4/1997 | Saab | |
| 5,630,426 A | 5/1997 | Eggers | |
| 5,672,153 A | 9/1997 | Lax et al. | |
| 5,707,349 A | 1/1998 | Edwards | |
| 5,728,094 A * | 3/1998 | Edwards | 606/41 |
| 5,769,846 A | 6/1998 | Edwards | |
| 5,792,140 A | 8/1998 | Tu et al. | |
| 5,797,903 A * | 8/1998 | Swanson et al. | 606/34 |
| 5,800,482 A | 9/1998 | Pomeranz | |
| 5,800,484 A * | 9/1998 | Gough et al. | 607/104 |
| 5,807,395 A * | 9/1998 | Mulier et al. | 606/41 |
| 5,817,092 A | 10/1998 | Behl | |
| 5,823,956 A | 10/1998 | Roth | |
| 5,879,348 A | 3/1999 | Owens et al. | |
| 5,891,134 A | 4/1999 | Goble et al. | |
| 5,921,982 A | 7/1999 | Lesh | |
| 5,947,964 A | 9/1999 | Eggers | |
| 5,951,546 A * | 9/1999 | Lorentzen | 606/41 |
| 5,961,513 A | 10/1999 | Swanson | |
| 5,967,984 A | 10/1999 | Chu | |
| 5,983,660 A | 11/1999 | Kiessel et al. | |
| 6,002,968 A | 12/1999 | Edwards | |
| 6,012,457 A | 1/2000 | Lesh | |
| 6,023,638 A | 2/2000 | Swanson | |
| 6,053,937 A * | 4/2000 | Edwards et al. | 607/104 |
| 6,106,521 A | 8/2000 | Blewett et al. | |
| 6,107,699 A | 8/2000 | Swanson | |
| 6,117,101 A | 9/2000 | Diederich et al. | |
| 6,142,994 A | 11/2000 | Swanson | |
| 6,152,920 A | 11/2000 | Thompson et al. | |
| 6,161,543 A | 12/2000 | Cox et al. | |
| 6,168,594 B1 | 1/2001 | LaFontaine | |
| 6,179,835 B1 | 1/2001 | Panescu et al. | |
| 6,212,433 B1 | 4/2001 | Behl | |
| 6,241,727 B1 | 6/2001 | Tu et al. | |
| 6,306,133 B1 | 10/2001 | Tu et al. | |
| 6,311,692 B1 | 11/2001 | Vaska et al. | |
| 6,314,962 B1 | 11/2001 | Vaska et al. | |
| 6,314,963 B1 | 11/2001 | Vaska et al. | |
| 6,358,246 B1 | 3/2002 | Behl et al. | |
| 6,419,653 B2 * | 7/2002 | Edwards et al. | 604/22 |
| 6,485,489 B2 | 11/2002 | Teirstein et al. | |
| 6,529,756 B1 | 3/2003 | Phan et al. | |
| 2003/0069570 A1 | 4/2003 | Witzel et al. | |

FOREIGN PATENT DOCUMENTS

| | | |
|---|---|---|
| WO | WO-00/29062 A2 | 5/2000 |
| WO | WO-00/56237 A2 | 9/2000 |
| WO | WO-01/37746 A1 | 5/2001 |

\* cited by examiner

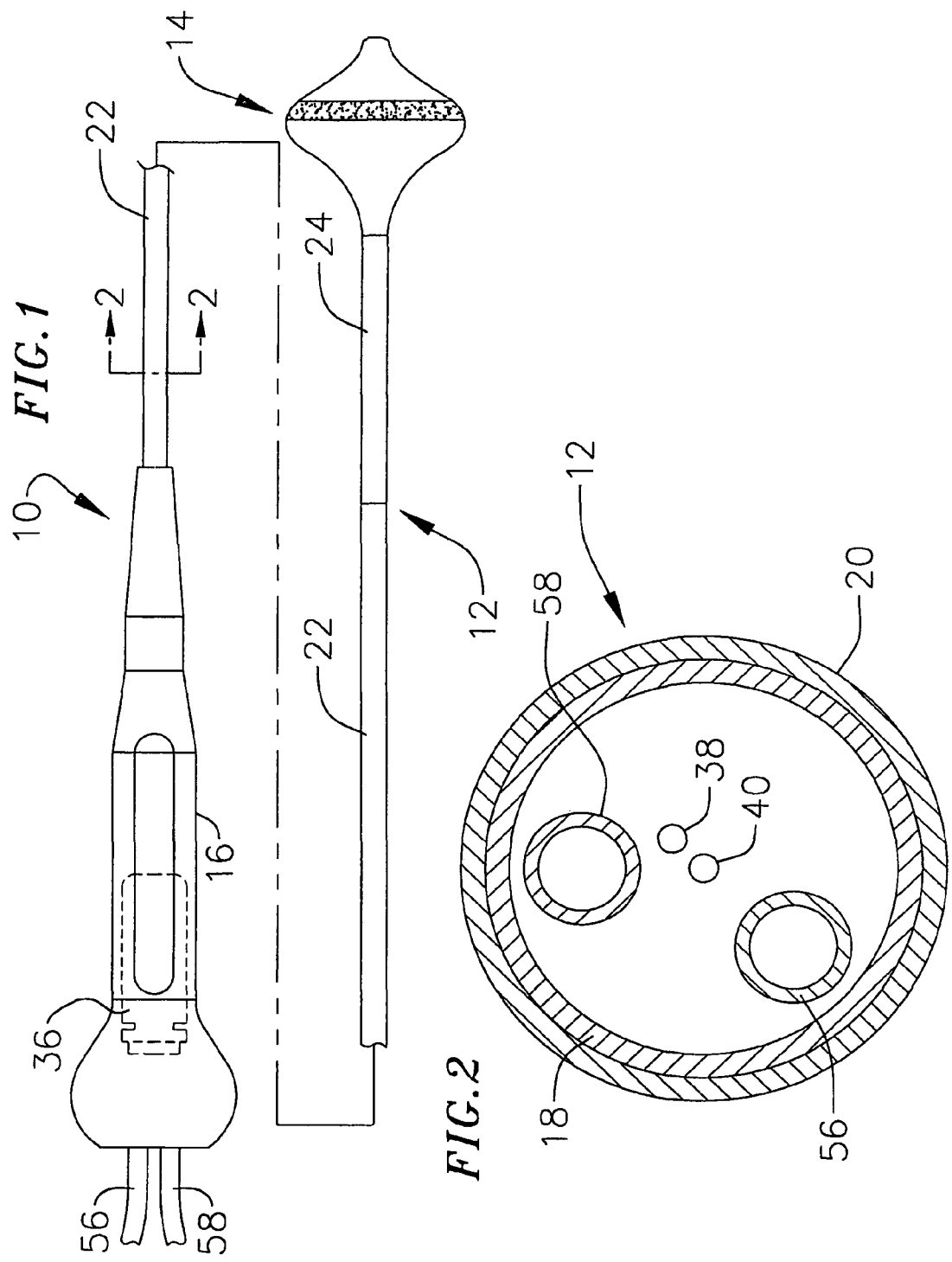

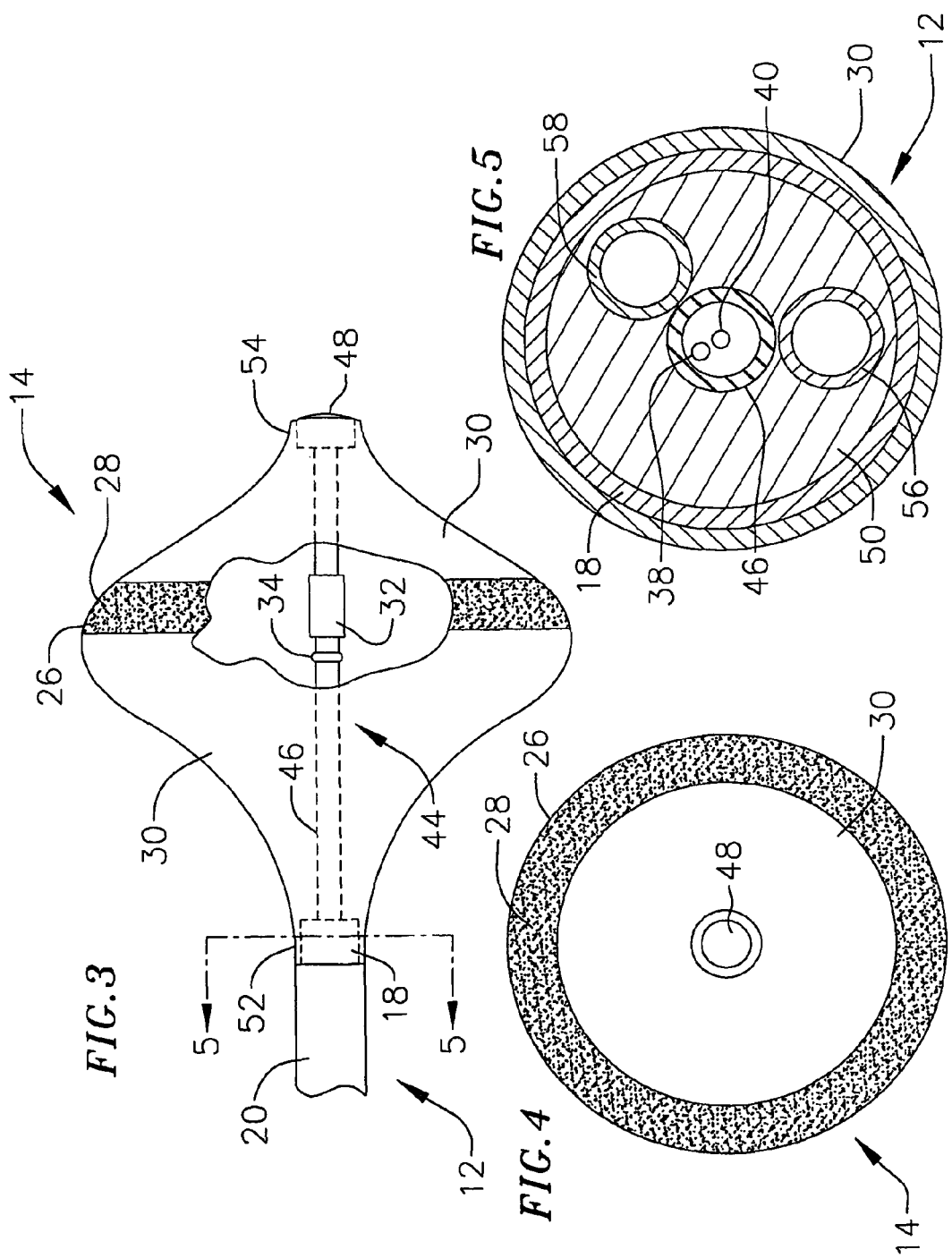

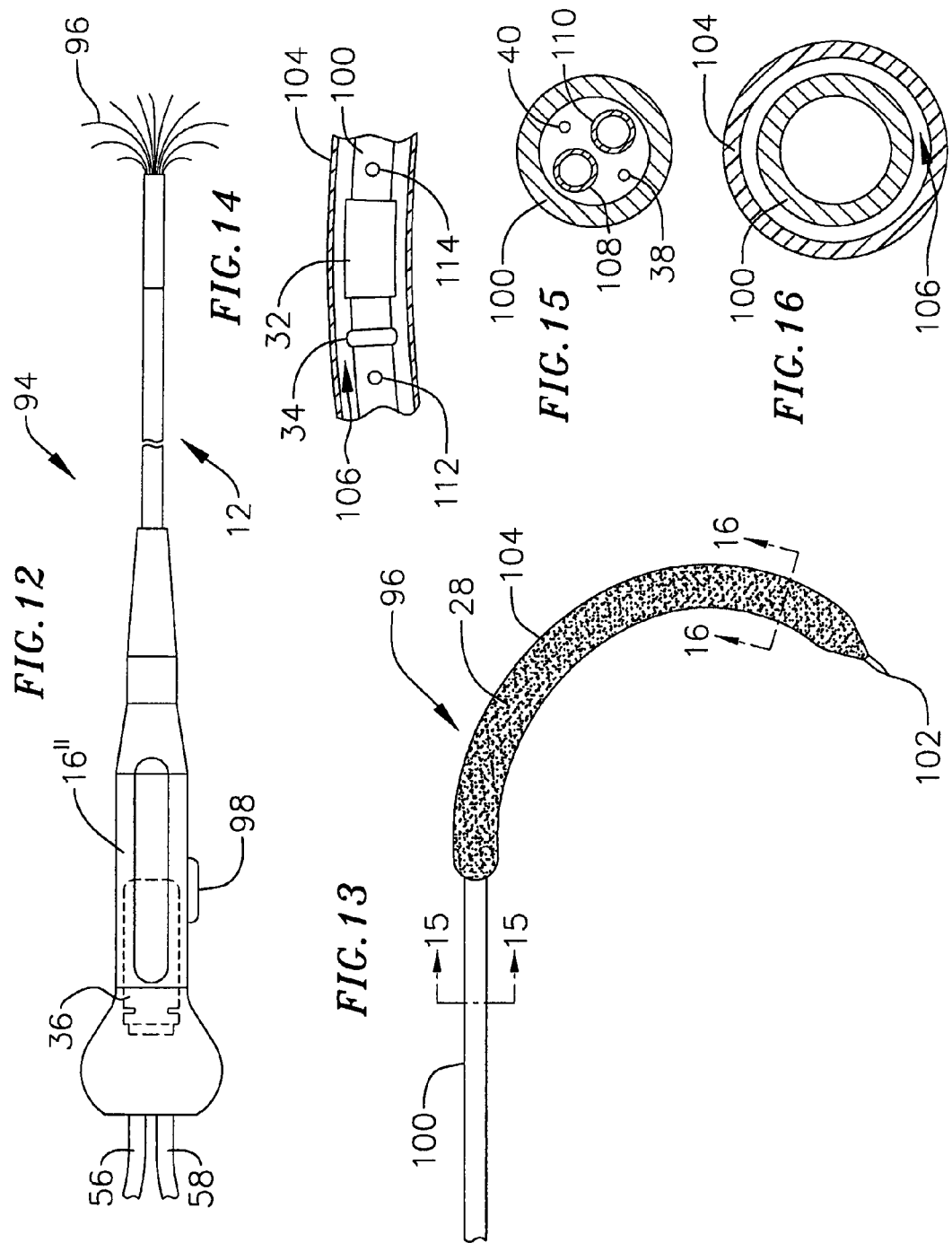

SURGICAL PROBE FOR SUPPORTING INFLATABLE THERAPEUTIC DEVICES IN CONTACT WITH TISSUE IN OR AROUND BODY ORIFICE AND WITHIN TUMORS

CROSS-REFERENCE TO RELATED APPLICATIONS

This application is a continuation of U.S. application Ser. No. 11/027,622, filed Dec. 30, 2004, which is a continuation of U.S. application Ser. No. 09/737,176, filed Dec. 13, 2000, now U.S. Pat. No. 6,837,885, which is a continuation-in-part of U.S. application Ser. No. 09/083,874, filed May 22, 1998, now U.S. Pat. No. 6,428,537, which is incorporated herein in its entirety.

BACKGROUND OF THE INVENTIONS

1. Field of Inventions

The present inventions relate generally to surgical probes that support therapeutic devices in contact with body tissue.

2. Description of the Related Art

There are many instances where diagnostic and therapeutic elements must be inserted into the body. One instance involves the treatment of cardiac conditions such as atrial fibrillation and atrial flutter which lead to an unpleasant, irregular heart beat, called arrhythmia.

Normal sinus rhythm of the heart begins with the sinoatrial node (or "SA node") generating an electrical impulse. The impulse usually propagates uniformly across the right and left atria and the atrial septum to the atrioventricular node (or "AV node"). This propagation causes the atria to contract in an organized way to transport blood from the atria to the ventricles, and to provide timed stimulation of the ventricles. The AV node regulates the propagation delay to the atrioventricular bundle (or "HIS" bundle). This coordination of the electrical activity of the heart causes atrial systole during ventricular diastole. This, in turn, improves the mechanical function of the heart. Atrial fibrillation occurs when anatomical obstacles in the heart disrupt the normally uniform propagation of electrical impulses in the atria. These anatomical obstacles (called "conduction blocks") can cause the electrical impulse to degenerate into several circular wavelets that circulate about the obstacles. These wavelets, called "reentry circuits," disrupt the normally uniform activation of the left and right atria.

Because of a loss of atrioventricular synchrony, the people who suffer from atrial fibrillation and flutter also suffer the consequences of impaired hemodynamics and loss of cardiac efficiency. They are also at greater risk of stroke and other thromboembolic complications because of loss of effective contraction and atrial stasis.

One surgical method of treating atrial fibrillation by interrupting pathways for reentry circuits is the so-called "maze procedure" which relies on a prescribed pattern of incisions to anatomically create a convoluted path, or maze, for electrical propagation within the left and right atria. The incisions direct the electrical impulse from the SA node along a specified route through all regions of both atria, causing uniform contraction required for normal atrial transport function. The incisions finally direct the impulse to the AV node to activate the ventricles, restoring normal atrioventricular synchrony. The incisions are also carefully placed to interrupt the conduction routes of the most common reentry circuits. The maze procedure has been found very effective in curing atrial fibrillation. However, the maze procedure is technically difficult to do.

Maze-like procedures have also been developed utilizing catheters which can form lesions on the endocardium (the lesions being 1 to 15 cm in length and of varying shape) to effectively create a maze for electrical conduction in a predetermined path. The formation of these lesions by soft tissue coagulation (also referred to as "ablation") can provide the same therapeutic benefits that the complex incision patterns that the surgical maze procedure presently provides.

Catheters used to create lesions typically include a relatively long and relatively flexible body portion that has a soft tissue coagulation electrode on its distal end and/or a series of spaced tissue coagulation electrodes near the distal end. The proximal end of the flexible body is typically connected to a handle which includes steering controls. The portion of the catheter body portion that is inserted into the patient is typically from 58.4 cm to 139.7 cm in length and there may be another 20.3 cm to 38.1 cm, including a handle, outside the patient. The length and flexibility of the catheter body allow the catheter to be inserted into a main vein or artery (typically the femoral artery), directed into the interior of the heart, and then manipulated such that the coagulation electrode contacts the tissue that is to be ablated. Linear and curvilinear lesions can then be created by dragging a single electrode or by applying power (preferably simultaneously) to the series of spaced electrodes.

Catheter-based soft tissue coagulation has proven to be a significant advance in the medical arts generally and in the treatment of cardiac conditions in particular. Nevertheless, the inventors herein have determined that catheter-based procedures are not appropriate in every situation and that conventional catheters are not capable of reliably forming all types of lesions. For example, one lesion that has proven to be difficult to form with conventional catheter devices is the circumferential lesion that is used to isolate the pulmonary vein and cure ectopic atrial fibrillation. Lesions that isolate the pulmonary vein may be formed within the pulmonary vein itself or in the tissue surrounding the pulmonary vein. These circumferential lesions are formed by dragging a tip electrode around the pulmonary vein or by creating a group of interconnected curvilinear lesions one-by-one around the pulmonary vein. Such techniques have proven to be less than effective because they are slow and gaps of conductive tissue can remain after the procedure. It can also be difficult to achieve the adequate tissue contact with conventional catheters.

Accordingly, the inventors herein have determined that a need exists for structures that can be used to create circumferential lesions within or around bodily orifices and, in the context of the treatment of atrial fibrillation, within or around the pulmonary vein.

Another instance where therapeutic elements are inserted into the body is the treatment of tumors, such as the cancerous tumors associated with breast cancer and liver cancer. Heretofore, tumors have been treated with highly toxic drugs that have proven to have severe side effects. More recently, devices including a plurality of needle-like electrodes have been introduced. The needle-like electrodes may be directed into the tumor tissue and used to deliver RF energy. The associated current flow heats the tissue and causes it to coagulate.

The inventors herein have determined that there are a number of shortcomings associated with the use of needle-like electrodes to coagulate tissue. Most notably, the needle-like electrodes produce non-uniform, shallow lesions and/or spot lesions and also fail to coagulate the entire volume of tumor tissue. This failure can ultimately result in the tumor growing to be even larger than its original size. The needle-like electrodes can also cause tissue charring. Moreover, tissue tends to shrink around the needle-like electrodes during the coagulation process. This makes it very difficult to withdraw the electrodes from the patient and often results in tissue trauma.

Accordingly, the inventors herein have determined that a need exists for a device that can completely and uniformly coagulate large volumes of tissue without charring and can also be removed from the patient without the difficulty associated with needle-like electrodes.

SUMMARY OF THE INVENTION

Accordingly, the general object of the present inventions is to provide a device that avoids, for practical purposes, the aforementioned problems. In particular, one object of the present inventions is to provide a device that can be used to create circumferential lesions in or around the pulmonary vein and other bodily orifices in a more efficient manner than conventional apparatus.

In order to accomplish some of these and other objectives, a surgical probe in accordance with one embodiment of a present invention includes a relatively short shaft and an inflatable therapeutic element associated with the distal portion of the shaft. In a preferred embodiment, the therapeutic element will be configured so that it can form a continuous lesion around a pulmonary vein.

Such a probe provides a number of advantages over conventional apparatus. For example, the present surgical probe may be used during open heart surgery or in less invasive procedures where access to the heart is obtained via a thoracostomy, thoracotomy or median sternotomy. The relatively short shaft and manner in which access is obtained allows the therapeutic element to be easily inserted into the heart and placed against the target tissue with the desired level of contact, thereby eliminating many of the problems associated with catheter-based procedures. Moreover, the present therapeutic element may be used to form lesions in an annular region of tissue within or around the pulmonary vein (or other orifice in other procedures) in one step, thereby eliminating the need to either drag a tip electrode around an annular region or form a number of interconnected curvilinear lesions that is associated with catheter-based procedures.

Additionally, in accordance with a preferred embodiment, the flexibility of the inflatable therapeutic element may be varied as appropriate. This allows the physician to achieve the appropriate level of tissue contact, even when the shaft is not perfectly perpendicular to the target tissue area, the target tissue area is somewhat uneven, or the target tissue has become rigid due to calcification.

In accordance with another preferred embodiment, the inflatable therapeutic element will be configured such that it can be inserted into a tumor (or other target location), inflated and then used to uniformly coagulate the entire tumor (or a large volume of tissue associate with the other location) without charring. Once the coagulation procedure is complete, the inflatable therapeutic element can be deflated and removed from patient without the difficulty and trauma associated with needle-like electrodes.

In order to accomplish some of these and other objectives, a surgical probe in accordance with one embodiment of a present invention includes hollow needle and a therapeutic assembly, located within the hollow needle and movable relative thereto, having a relatively short shaft and an inflatable therapeutic element associated with the distal portion of the shaft. The hollow needle may be used to pierce through tissue to enter a target location such as a tumor. Prior to coagulation, the hollow needle may be withdrawn and the inflatable therapeutic element held in place within the tumor. The therapeutic element may then be inflated and the tissue coagulated. When the coagulation procedure is complete, the therapeutic element may be deflated and withdrawn back into the hollow needle.

In order to accomplish some of these and other objectives, a surgical probe in accordance with one embodiment of a present invention includes one or more needles having inflatable porous therapeutic elements mounted thereon. The needles may be directed into tissue, such as tumor tissue for example, in a manner similar to conventional needle electrodes. Here, however, conductive fluid within the inflatable porous therapeutic elements will draw heat away from the therapeutic element and the adjacent tissue. Such heat transfer results in the formation of relatively deep, large volume lesions without the charring and coagulation associated with conventional needle electrodes.

The above described and many other features and attendant advantages of the present inventions will become apparent as the inventions become better understood by reference to the following detailed description when considered in conjunction with the accompanying drawings.

BRIEF DESCRIPTION OF THE DRAWINGS

Detailed description of preferred embodiments of the inventions will be made with reference to the accompanying drawings.

FIG. 1 is a side view of a surgical probe in accordance with a preferred embodiment of a present invention.

FIG. 2 is a section view taken along line 2-2 in FIG. 1.

FIG. 3 is a cutaway view of the distal portion of the exemplary surgical probe illustrated in FIG. 1.

FIG. 4 is a front view of the exemplary surgical probe illustrated in FIG. 1.

FIG. 5 is a section view taken along line 5-5 in FIG. 3.

FIG. 12 is a side view of a surgical probe in accordance with a preferred embodiment of a present invention.

FIG. 13 is an enlarged view of one of the needles in the surgical probe illustrated in FIG. 12.

FIG. 14 is a partial section view of a portion of one of the needles in the surgical probe illustrated in FIG. 12.

FIG. 15 is a section view taken along line 15-15 in FIG. 13.

FIG. 16 is a section view taken along line 16-16 in FIG. 13.

DETAILED DESCRIPTION OF THE PREFERRED EMBODIMENTS

Figure 6:
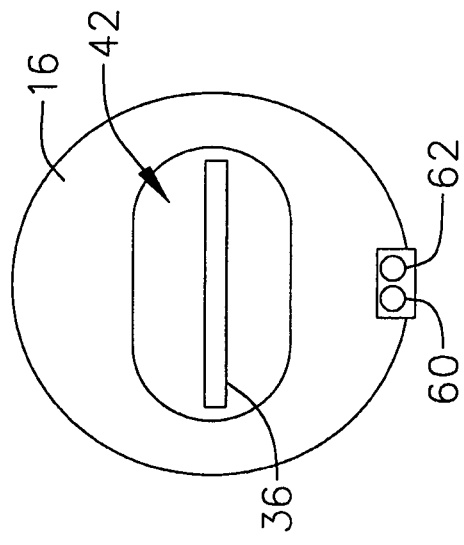
FIG. 6 is rear view of the exemplary surgical probe illustrated in FIG. 1 with the fluid lumens removed.
Figure 7:
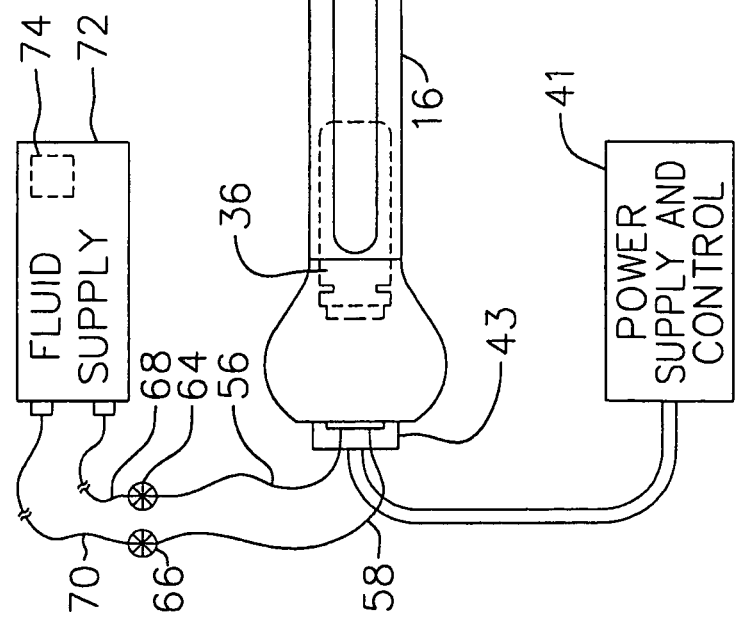
FIG. 7 is a side view showing the exemplary surgical probe illustrated in FIG. 1 connected to a fluid supply and a power supply.

The following is a detailed description of the best presently known modes of carrying out the inventions. This description is not to be taken in a limiting sense, but is made merely for the purpose of illustrating the general principles of the inventions.

This specification discloses a number of probe structures, mainly in the context of cardiac ablation, because the structures are well suited for use with myocardial tissue. For example, the present inventions are designed to produce intimate tissue contact with target substrates associated with arrhythmias such as atrial fibrillation. One application is the creation of lesions within or around the pulmonary vein to treat ectopic atrial fibrillation. Nevertheless, it should be appreciated that the structures are applicable for use in therapies involving other types of soft tissue. For example, various aspects of the present inventions have applications in procedures concerning other regions of the body such as the prostate, liver, brain, gall bladder, uterus and other solid organs.

As illustrated for example in FIGS. 1-7, a surgical probe 10 in accordance with a preferred embodiment of a present invention includes a relatively short shaft 12, an inflatable therapeutic element 14 and a handle 16. The relatively short shaft 12 will typically be between 10.1 cm and 45.7 cm in length, and is preferably about 17.8 cm in length, while the outer diameter of the shaft is preferably between about 6 and 24 French.

Force is applied through the shaft 12 in order to achieve the appropriate level of tissue contact. Thus, the shaft 12 should be sufficiently strong to prevent collapse when the force is applied and is preferably relatively stiff. As used herein the phrase "relatively stiff" means that the shaft 12 (or other structural element) is either rigid, malleable, or somewhat flexible. A rigid shaft cannot be bent. A malleable shaft is a shaft that can be readily bent by the physician to a desired shape, without springing back when released, so that it will remain in that shape during the surgical procedure. Thus, the stiffness of a malleable shaft must be low enough to allow the shaft to be bent, but high enough to resist bending when the forces associated with a surgical procedure are applied to the shaft. A somewhat flexible shaft will bend and spring back when released. However, the force required to bend the shaft must be substantial. Rigid and somewhat flexible shafts are preferably formed from stainless steel, while malleable shafts are formed from fully annealed stainless steel.

In the illustrated embodiment, the shaft 12 consists of a hypotube 18 with an outer polymer jacket 20 and includes a proximal portion 22 and a distal portion 24, both of which are malleable. The proximal portion 22 is, however, stiffer than the distal portion 24. The proximal portion 22 is also longer (about 11.5 cm) than the distal portion 24 (about 6.4 cm).

One method of quantifying the flexibility of a shaft, be it shafts in accordance with the present inventions or the shafts of conventional catheters, is to look at the deflection of the shaft when one end is fixed in cantilever fashion and a force normal to the longitudinal axis of the shaft is applied somewhere between the ends. Such deflection ($\sigma$) is expressed as follows:

$$\sigma = WX^2(3L-X)/6EI$$

where:
W is the force applied normal to the longitudinal axis of the shaft,
L is the length of the shaft,
X is the distance between the fixed end of the shaft and the applied force,
E is the modulous of elasticity, and
I is the moment of inertia of the shaft.
When the force is applied to the free end of the shaft, deflection can be expressed as follows:

$$\sigma = WL^3/3EI$$

Assuming that W and L are equal when comparing different shafts, the respective E and I values will determine how much the shafts will bend. In other words, the stiffness of a shaft is a function of the product of E and I. This product is referred to herein as the "bending modulus." E is a property of the material that forms the shaft, while I is a function of shaft geometry, wall thickness, etc. Therefore, a shaft formed from relatively soft material can have the same bending modulus as a shaft formed from relatively hard material, if the moment of inertia of the softer shaft is sufficiently greater than that of the harder shaft.

For example, a relatively stiff 5.1 cm shaft (either malleable or somewhat flexible) would have a bending modulus of at least approximately 28 N-cm$^2$ (1 lb.-in.$^2$). Preferably, a relatively stiff 5.1 cm shaft will have a bending modulus of between approximately 86 N-cm$^2$ (3 lb.-in.$^2$) and approximately 1435 N-cm$^2$ (50 lb.-in.$^2$). By comparison, 5.1 cm piece of a conventional catheter shaft, which must be flexible enough to travel through veins, typically has bending modulus between approximately 2.8 N-cm$^2$ (0.11b.-in.$^2$) and approximately 8.6 N-cm$^2$ (0.3 lb.-in.$^2$). It should be noted that the bending modulus ranges discussed here are primarily associated with initial deflection. In other words, the bending modulus ranges are based on the amount of force, applied at and normal to the free end of the longitudinal axis of the cantilevered shaft, that is needed to produce 2.5 cm of deflection from an at rest (or no deflection) position.

As noted above, the deflection of a shaft depends on the composition of the shaft as well as its moment of inertia. The shaft could be made of polymeric material, metallic material or a combination thereof. By designing the shaft 12 to be relatively stiff (and preferably malleable), the present surgical probe is better adapted to the constraints encountered during the surgical procedure. The force required to bend a relatively stiff 5.1 cm long shaft should be in the range of approximately 6.7 N (1.5 lbs.) to approximately 53.4 N (12 lbs.). By comparison, the force required to bend a 5.1 cm piece of conventional catheter shaft should be between approximately 0.9 N (0.2 lb.) to 1.1 N (0.25 lb.). Again, such force values concern the amount of force, applied at and normal to the free end of the longitudinal axis of the cantilevered shaft, that is needed to produce 2.5 cm of deflection from an at rest (or no deflection) position.

Ductile materials are preferable in many applications because such materials can deform plastically before failure. Materials are classified as either ductile or brittle, based upon the percentage of elongation before failure. A material with more than 5 percent elongation prior to fracture is generally considered ductile, while a material with less than 5 percent elongation prior to fracture is generally considered brittle.

Alternatively, the shaft 12 could be a mechanical component similar to shielded (metal spiral wind jacket) conduit or flexible Loc-Line®, which is a linear set of interlocking ball and socket linkages that can have a center lumen. These would be hinge-like segmented sections linearly assembled to make the shaft.

Turning to FIGS. 3 and 4, the exemplary inflatable therapeutic element 14 is formed from an electrically non-conductive or semi-conductive thermoplastic or thermosetting plastic material and includes a forward facing porous region 26 having micropores 28 and non-porous regions 30. Fluid pressure is used to inflate the therapeutic element 14 and maintain it in its expanded state in the manner described below. The fluid used to fill the therapeutic element 14 is an electrically conductive fluid that establishes an electrically conductive path to convey RF energy from the porous region 26 to tissue.

Although other shapes (such as oval, triangular and rectangular) and sizes may be employed, the exemplary inflatable therapeutic element 14 is substantially circular in cross section has a diameter between about 1.0 cm to about 3.0 cm at its widest point when inflated. A preferred inflated diameter is about 1.5 cm. The forward facing porous region 26, which will have a width of about 1 mm to about 6 mm, is perpendicular to the longitudinal axis of the shaft 12. Such shapes and sizes are well suited for use with pulmonary veins because they allow the porous region 26 to be placed directly in contact with the targeted tissue area by a physician during open heart surgery. Nevertheless, other inflatable therapeutic element configurations, such as those where the entire forward facing half is porous, a solid circular portion of the forward facing half is porous, or the entire element is porous, may be employed as applications dictate.

Referring more specifically to FIG. 3, an electrode 32 is carried within the exemplary inflatable therapeutic element 14. The electrode 32 should be formed from material with both relatively high electrical conductivity and relatively high thermal conductivity. Suitable materials for the electrode 32, the length of which preferably ranges from about 1 mm to 6 mm, include gold, platinum, and platinum/iridium. Noble metals are preferred. The micropores 28 establish ionic transport of the tissue coagulating energy from the electrode 32 through the electrically conductive fluid to tissue outside the therapeutic element 14.

The electrically conductive fluid preferably possesses a low resistivity to decrease ohmic loses and thus ohmic heating effects within the therapeutic element 14. The composition of the electrically conductive fluid can vary. A hypertonic saline solution, having a sodium chloride concentration at or near saturation, which is about 20% weight by volume is preferred. Hypertonic saline solution has a low resistivity of only about 5 ohm-cm, compared to blood resistivity of about 150 ohm-cm and myocardial tissue resistivity of about 500 ohm-cm. Alternatively, the fluid can be a hypertonic potassium chloride solution. This medium, while promoting the desired ionic transfer, requires closer monitoring of the rate at which ionic transport occurs through the micropores 28, to prevent potassium overload. When hypertonic potassium chloride solution is used, it is preferred to keep the ionic transport rate below about 1 mEq/min.

Due largely to mass concentration differentials across the micropores 28, ions in the conductive fluid will pass into the pores because of concentration differential-driven diffusion. Ion diffusion through the micropores 28 will continue as long as a concentration gradient is maintained across the therapeutic element 14. The ions contained in the micropores 28 provide the means to conduct current across the therapeutic element 14. When RF energy is conveyed from a RF power supply and control apparatus to the electrode 32, electric current is carried by the ions within the micropores 28. The RF currents provided by the ions result in no net diffusion of ions, as would occur if a DC voltage were applied, although the ions do move slightly back and forth during the RF frequency application. This ionic movement (and current flow) in response to the applied RF field does not require perfusion of fluid through the micropores 28. The ions convey RF energy through the micropores 28 into tissue to a return electrode, which is typically an external patch electrode (forming a unipolar arrangement). Alternatively, the transmitted energy can pass through tissue to an adjacent electrode (forming a bipolar arrangement). The RF energy heats tissue (mostly ohmically) to coagulate the tissue and form a lesion.

The temperature of the fluid is preferably monitored for power control purposes. To that end, a thermistor 34 may be mounted within the exemplary therapeutic element 14. Other temperature sensing devices, such as a thermocouple and reference thermocouple arrangement, may be employed in place of or in addition to the thermistor 34. As illustrated for example in FIGS. 1-3, 6 and 7, the electrode 32 and thermistor 34 are respectively connected to an electrical connector 36 in the handle 16 by conductors 38 and 40 which extend through the shaft 12. The probe 10 may be connected to a suitable RF power supply and control apparatus 41 by a connector 43 that mates with the electrical connector 36. The handle 16 is provided with an opening 42 for this purpose.

The exemplary probe 10 may operate using a relatively simple control scheme wherein lesions are formed by supplying power to the electrode 32 at a predetermined level for a predetermined period of time. When forming pulmonary vein lesions, for example, about 35 watts for a period of about 120 seconds is preferred. Should the temperature within the inflatable therapeutic element 14 exceed 90° C., power will be cut off by the control apparatus 41.

Accurate placement of the therapeutic element 14, particularly the porous region 26, is also important and color may be used to make it easier for the physician to accurately position the therapeutic element. The porous region 26 may be one color while the non-porous regions 30 may be another color. Alternatively, or in addition, the porous region 26 may be relatively clear and the non-porous regions 30 may be relatively opaque. These properties may also be reversed. In one exemplary implementation, the porous region 26 may be substantially clear and colorless, while the non-porous regions 30 may be a relatively opaque blue color. This arrangement results in the porous region 26 being a clear, colorless ring that is readily visible to the physician.

The exemplary therapeutic element 14 is provided with a stabilizing structure 44 (FIG. 3). The stabilizing structure 44 preferably includes a flexible, non-conductive tubular member 46 and a tip member 48 on the distal end of the tubular member. The flexibility of the tubular member 46, which supports the electrode 32 and thermistor 34 and also provides passage for the conductors 38 and 40, prevents tissue perforation. Tip member 48 includes a blunt distal surface that prevents tissue perforation. During assembly, the proximal end of the tubular member 46 may be secured within the distal end of the shaft 12 with a suitable adhesive material 50 (such as cyanoacrylate) in the manner illustrated in FIG. 5.

The exemplary therapeutic element 14 illustrated in FIG. 3 is molded such that the inner diameter of its proximal end 52 closely corresponds to the outer diameter of the shaft 12 and the inner diameter of its distal end 54 closely corresponds to the outer diameter of tip member 48. The polymer coating 20 may be removed from the distal tip of the shaft 12 prior to assembly (as shown) or left in place and the therapeutic element proximal end 52 positioned thereover. Cyanoacrylate or another suitable adhesive material may be used to secure the therapeutic element proximal and distal ends 52 and 54 in place and provide fluid tight seals.

With respect to materials, the porous region 26 is preferably formed from regenerated cellulose or a microporous elastic polymer. Hydro-Fluoro M material is another exemplary material. Materials such as nylons (with a softening temperature above 100° C.), PTFE, PEI and PEEK that have micropores created through the use of lasers, electrostatic discharge, ion beam bombardment or other processes may also be used. Such materials would preferably include a hydrophilic coating. The micropores should be about 1 to 5 μm in diameter and occupy about 1% of the surface area of the porous region 26. A slightly larger pore diameter may be employed. Because the larger pore diameter would result in significant fluid transfer through the porous region, a saline solution having a sodium chloride concentration of about 0.9% weight by volume is preferred.

The non-porous regions are preferably formed from relatively elastic materials such as silicone and polyisoprene. However, other less elastic materials, such as Nylon®, Pebax®, polyethylene, polyesterurethane and polyester, may also be used. Here, the inflatable therapeutic element 14 may be provided with creased regions that facilitate the collapse of the porous electrode.

Additional information and examples of expandable and collapsible bodies are disclosed in U.S. patent application Ser. No. 08/984,414, entitled "Devices and Methods for Creating Lesions in Endocardial and Surrounding Tissue to Isolate Arrhythmia Substrates," U.S. Pat. No. 5,368,591, and U.S. Pat. No. 5,961,513, each of which is incorporated herein by reference.

The therapeutic element 14 will typically be filled with conductive fluid prior to insertion of the surgical probe 10 into the patient. As illustrated for example in FIGS. 2, 5, 6 and 7, the conductive fluid is supplied under pressure to the inflatable therapeutic element 14 by way of an infusion lumen 56. The fluid exits the therapeutic element 14 by way of a ventilation lumen 58. The infusion and ventilation lumens 56 and 58 extend from the distal end of the shaft 12 and through a pair of apertures 60 and 62 in the handle 16. The proximal ends of the infusion and ventilation lumens 56 and 58 are provided with on-off valves 64 and 66, which may be connected to the infusion and ventilation lines 68 and 70 of a fluid supply device 72 such as, for example, an infusion pump capable of variable flow rates.

In a preferred implementation, the conductive fluid is continuously infused and ventilated (at a rate of about 4-8 mils/minute for a therapeutic element 14 that is about 1.5 cm in diameter). Thus, in addition to inflating the therapeutic element 14 and providing a conductive path from the electrode 32 to the tissue, the fluid cools the therapeutic element so that heat is only generated within the tissue by virtue of the passage of current therethrough.

The pressure of the fluid supplied by the fluid supply device 72 within the therapeutic element 14 should be relatively low (less than 20 psi) and may be varied by the fluid supply device in accordance with the desired level of inflation, strength of materials used and the desired degree of flexibility. The pressure, which is a function of the fluid flow rate, may be increased by increasing the fluid flow rate and decreased by decreasing the fluid flow rate. The desired pressure may be input into the fluid supply device 72 and pressure regulation may be performed automatically by a controller within the fluid supply device which varies the flow rate as appropriate. Alternatively, the flow rate (and pressure) may be varied manually by the physician.

Pressure within the therapeutic element 14 may be monitored in a variety of ways. For example, flow through the infusion and ventilation lumens 56 and 58 may be cut off for a brief period (about 1 second) so that the fluid pressure can be measured by a pressure sensor 74 associated with the fluid supply device 72 (as shown) or with one of the valves 64 and 66. Alternatively, a pressure sensor lumen (not shown) that is filled with non-flowing fluid and extends from the interior of the therapeutic element 14 to the pressure sensor 74 associated with the fluid supply device 72, or to a pressure sensor associated with one of the valves 64 and 66, may be used without cutting off the fluid flow.

Varying the level of pressure within the therapeutic element 14 allows the physician to achieve the appropriate level of tissue contact, even when the shaft 14 is not perfectly perpendicular to the target tissue area and when the target tissue area is somewhat uneven. For example, a stiffer therapeutic element 14 (which distorts the tissue) would be preferred when the pulmonary vein ostium is relatively circular and when the ostium tissue is relatively healthy and pliable. A more flexible therapeutic element 14 (which conforms to the tissue) would be preferred when the ostium is not circular and the ostium tissue is relatively calcified and rigid due to disease. The ability to vary the stiffness allows the physician to easily form a lesion that extends completely around the pulmonary vein or other bodily orifice by simply inserting the distal portion of the probe 10 into the patient, positioning the therapeutic element 14 in or around the bodily orifice, and applying power.

Figure 8:
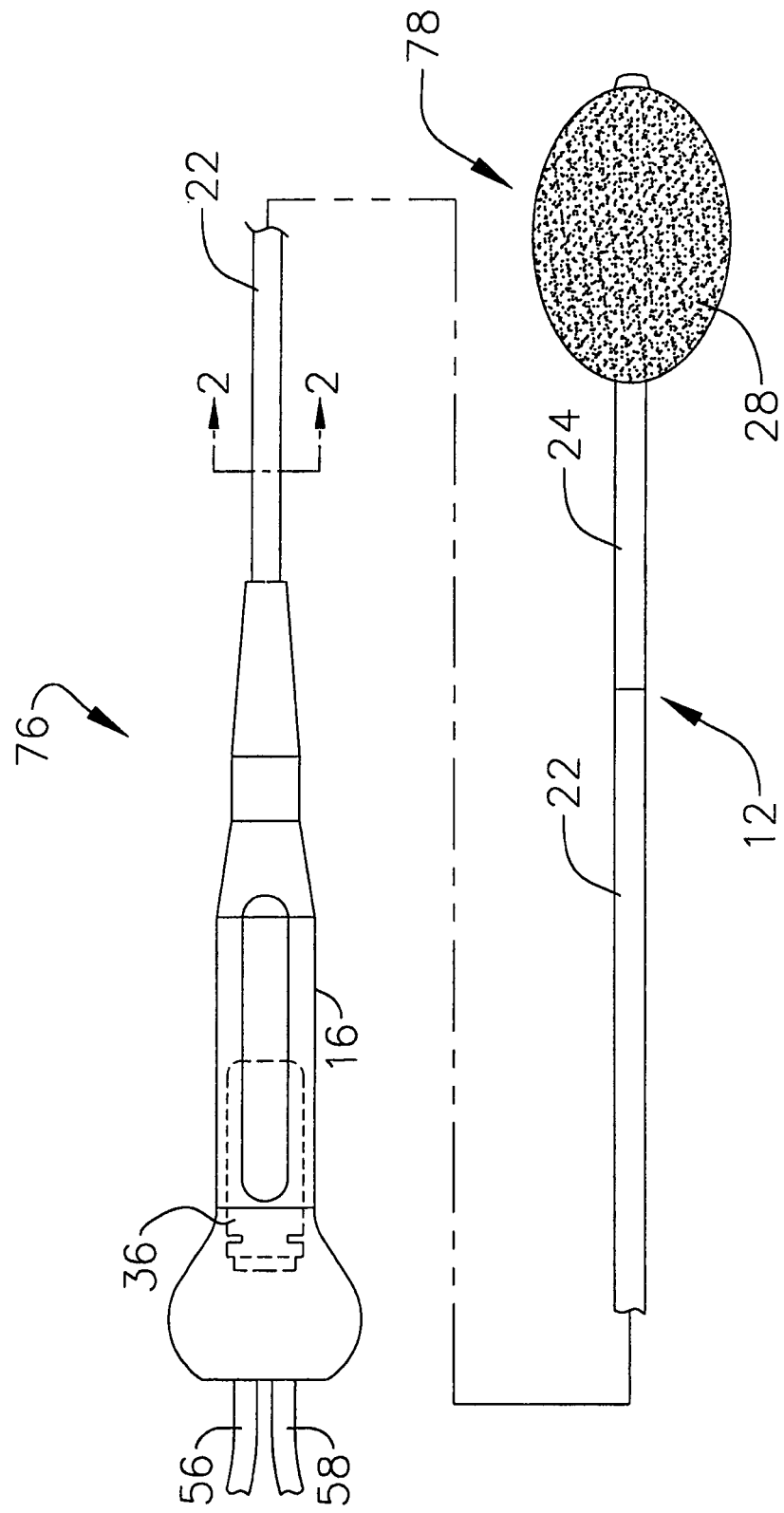
FIG. 8 is a side view of a surgical probe in accordance with a preferred embodiment of a present invention.

The present inventions are, of course, applicable to therapies in areas other than the treatment of atrial fibrillation. One such therapy is the treatment of tumors, such as the cancerous tumors associated with breast cancer and liver cancer. One example of a surgical probe that is well suited for the treatment of tumors is illustrated in FIG. 8 and generally represented by reference numeral 76. Surgical probe 76 is substantially identical to the probe 10 illustrated in FIGS. 1-7. Here, however, the probe includes a therapeutic element 78 that is formed from the same material as microporous region 26 and is entirely covered with micropores 28. Although the size and shape will vary in accordance with the intended application, the exemplary therapeutic element 78 is approximately 5 mm to 50 mm in length and has a diameter of about 10 mm to 40 mm when inflated.

The exemplary surgical probe 76 illustrated in FIG. 8 may be introduced to a target location, such as within a cancerous tumor, using a variety of techniques. Such techniques include laparoscopic techniques where the probe will be introduced with a trocar, radially expandable port, or step trocar expandable port. The therapeutic element 78 should be deflated during the introduction process. Once the therapeutic element 78 is at the target location, it may be inflated and the tissue coagulated in the manner described above. The therapeutic element 78 will be deflated and removed from the patient by way of the trocar, radially expandable port, or step trocar expandable port when the coagulation procedure is complete.

The exemplary therapeutic element 78, as well as the other therapeutic elements described below that are intended to be expanded within the tissue of solid organ tissue or expanded within other tissue (see FIGS. 9, 10 and 12-16), may include larger pores than therapeutic elements that are expanded prior to use or expanded within a hollow region inside an organ or other portion of the body. Pore sizes up to 0.1 mm are acceptable. The larger pore sizes may be used because the tight fit between the tissue and the inflated therapeutic element that results from the inflation of the therapeutic element within solid tissue increases the effective flow resistance through the pores 28. Additionally, the small amount of electrically conductive fluid leakage that may be associated with the use of larger pores will decrease ohmic losses and allow power to be increased without tissue charring and vaporization.

Figure 9:
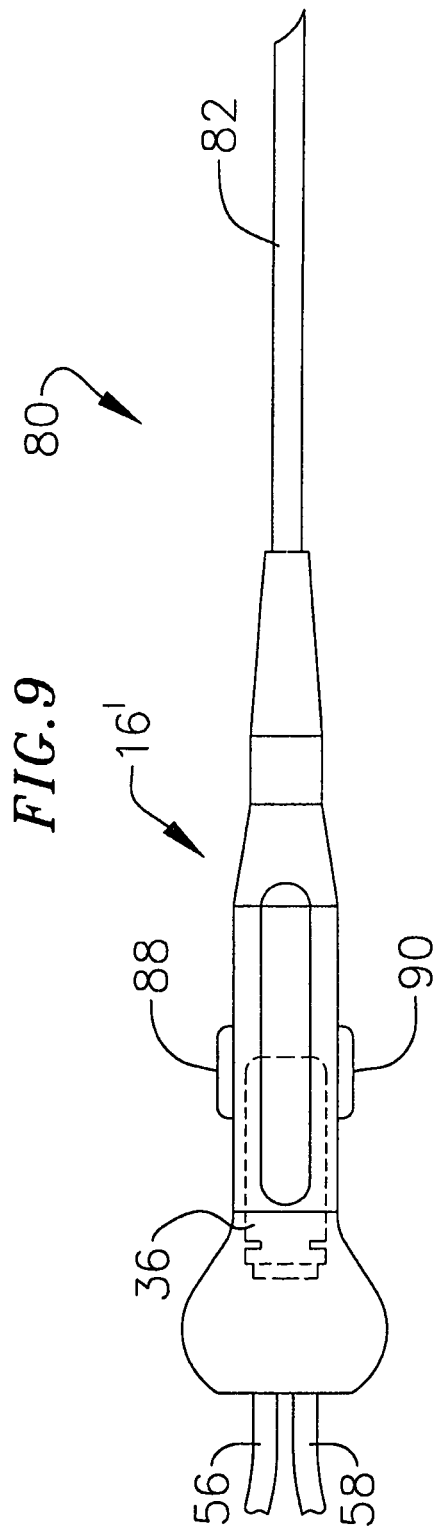
FIG. 9 is a side view of a surgical probe in accordance with a preferred embodiment of a present invention.
Figure 10:
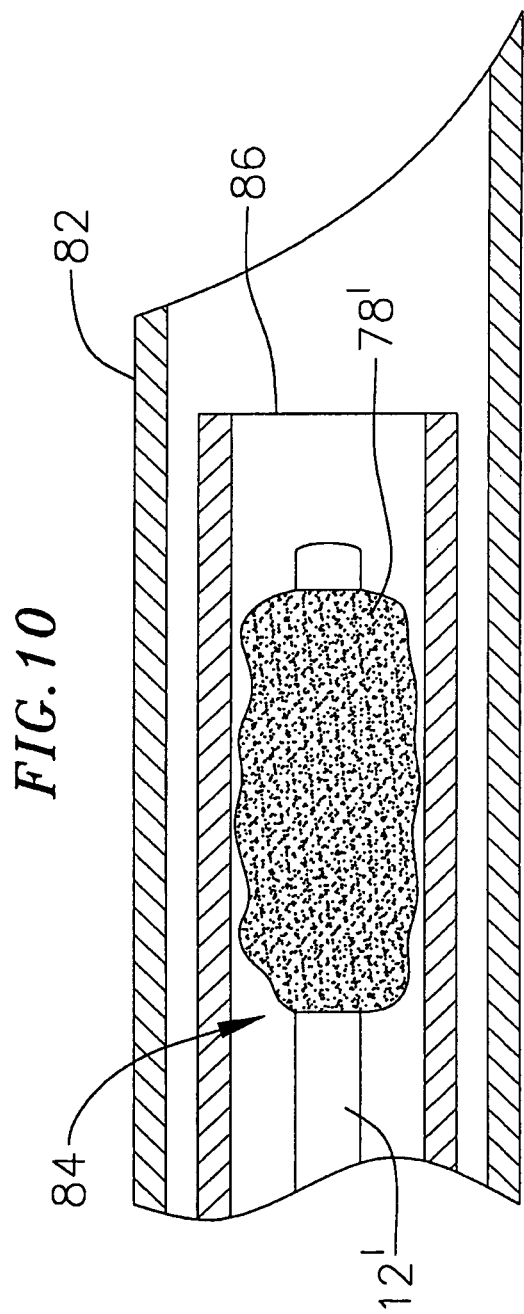
FIG. 10 is a partial section view of the distal portion of the surgical probe illustrated in FIG. 9.

Although its uses are not so limited, the exemplary surgical probe 80 illustrated in FIGS. 9 and 10 is also particularly well suited for treating tumors. Surgical probe 80 includes a hollow needle 82, a movable therapeutic assembly 84 that consists of a shaft 12' and a therapeutic element 78', and a movable stylet 86 that protects the therapeutic element. The therapeutic assembly 84 and stylet 86 may be independently moved proximally and distally relative to the hollow needle 82 with slidable knobs 88 and 90 mounted on the handle 16'.

Surgical probe 80 may be introduced into the patient through a trocar or any appropriate port and the hollow needle 82 used to pierce through tissue and enter a target location such as a tumor. The hollow needle 82 may, alternatively, be used to introduce the surgical probe 80 into the patient as well as to pierce through tissue and enter the target location. In either case, once within the tumor or other target location, the hollow needle 82 and stylet 86 may be withdrawn while the therapeutic assembly 84 is held in place so that the therapeutic element 78' will remain within the target location. The therapeutic element 78' may then be inflated and the tissue associated with the target location coagulated in the manner described above. Once the coagulation procedure is complete, the therapeutic element 78' will be deflated so that the stylet 86 can be slid over the therapeutic element. Both will then be pulled back into the hollow needle 82 so that the probe 80 can be removed from the patient.

The size, shapes and materials used to form the hollow needle 82, therapeutic assembly 84 and stylet 86 will vary in accordance with the intended application.

With respect to tumor treatment, the exemplary hollow needle 82 is preferably linear, is between about 1.3 cm and 7.6 cm in length, and has an outer diameter that is between about 2.0 mm and 6.4 mm and an inner diameter that is between about 1.5 mm and 5.8 mm. Suitable materials for the hollow needle 82, which is preferably either straight or has a preset curvature, include stainless steel and Nitinol. The shaft 12' is preferably straight (although it can have a curvature) and rigid (although it may be malleable) and the stiffness is uniform from one end to the other. Suitable materials include stainless steel, Nitinol and rigid polymers. The diameter is preferably between about 0.6 mm and 4.6 mm. The exemplary therapeutic element 78' is approximately 19 mm to 38 mm in length, a diameter of about 5 mm and 40 mm when inflated, with a wall thickness of about 0.025 mm to 0.250 mm. The stylet 86 may be formed from materials such as stainless steel and Nitinol and preferably has an outer diameter that is between about 1.4 mm and 5.7 mm and an inner diameter that is between about 1.1 mm and 5.2 mm.

Figure 11:
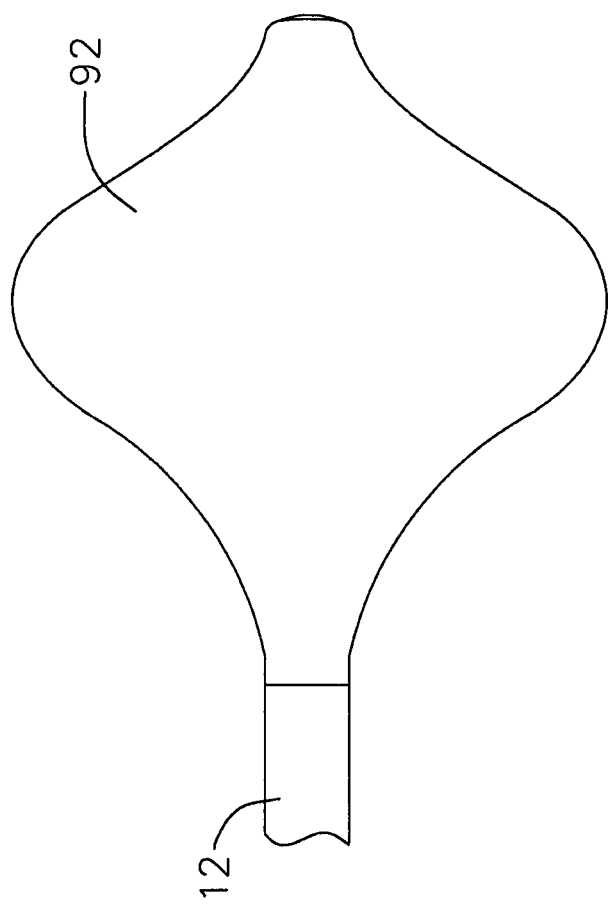
FIG. 11 is a side view of the distal portion of a surgical probe in accordance with a preferred embodiment of a present invention.

Turning to FIG. 11, surgical probes in accordance with other embodiments of the present inventions, which are otherwise substantially identical to the probe 10 illustrated in FIGS. 1-7, may include a heated inflatable therapeutic element 92 in place of the porous therapeutic element 14. The exemplary therapeutic element 92, which is supported on the distal end of the shaft 12 in essentially the same manner as therapeutic element 14, can be inflated with water, hypertonic saline solution, or other biocompatible fluids. The fluid may be supplied under pressure to the therapeutic element 92 by the fluid supply device 72 in the manner described above. The pressure should be relatively low (less than 20 psi) and will vary in accordance with the desired level of inflation, strength of materials used and the desired level of flexibility. The fluid will preferably be continuously infused and ventilated for cooling purposes. Alternatively, the fluid may instead fill the therapeutic element, remain there to be heated, and then be ventilated after the lesion formation procedure has been completed.

A fluid heating element is located within the therapeutic element 92. The fluid heating element is preferably an electrode (not shown) that may be formed from metals such as platinum, gold and stainless steel and mounted on the support structure 44. A bi-polar pair of electrodes may, alternatively, be used to transmit power through a conductive fluid, such as isotonic saline solution, to generate heat. The temperature of the fluid may be heated to about 90° C., thereby raising the temperature of the exterior of the therapeutic element 92 to approximately the same temperature for tissue coagulation. It should be noted, however, that the therapeutic element 92 tends to produce relatively superficial lesions.

Suitable materials for the exemplary therapeutic element 92 include relatively elastic thermally conductive biocompatible materials such as silicone and polyisoprene. Other less elastic materials, such as Nylon®, Pebax®, polyethylene and polyester, may also be used. Here, the therapeutic element 92 will have to be formed with fold lines. A temperature sensing element may also be provided. The heating electrode and temperature sensing element will be connected to the electrical connector 36 in the handle 18 by electrical conductors in the manner described above. Suitable power supply and control devices, which control power to based on a sensed temperature, are disclosed in U.S. Pat. Nos. 5,456,682, 5,582,609 and 5,755,715.

The exemplary therapeutic element 92 may also be used in conjunction with the surgical probes illustrated in FIGS. 8-10.

As illustrated for example in FIGS. 12-16, a surgical probe 94 in accordance with a preferred embodiment of a present invention includes a plurality of tissue penetrating needles 96 that may be advanced outwardly from, and retracted back into, the distal end of a shaft 12 with a slidable knob 98. The number of needles 96, which may be glued, clamped or otherwise secured to the slidable knob 98, preferably ranges from 1 to 25. Each of the needles 96 includes a main body 100, a sharpened tip 102 and an inflatable porous therapeutic element 104 with micropores 28. The materials used to form the therapeutic element 104, as well as the conductive fluid used therewith, are the same as those described above with respect to the porous region 26. Hydro-Fluoro M material may also be used. When inflated, a fluid circulation space 106 is defined between the main body 100 and the therapeutic element 104. An electrode 32 and a thermistor 34, which are positioned on the main body 100 within the space 106, are connected to the electrical connector 36 by conductors 38 and 40.

Although other configurations may be employed, the exemplary tissue penetrating needles 96 preferably have the preset curvature illustrated in FIG. 13 and will assume this curvature when they are advanced outwardly from the distal end of the shaft 12. To that end, suitable shape-memory materials for the needles 96 include stainless steel and Nitinol. It should be noted that the needles 96 do not each have to have the same curvatures or to even be curved at all. The needles 96 are preferably about 0.25 mm to 1.25 mm in diameter and the curved region is about 2.5 cm in length, while the diameter of the porous therapeutic element 104 is about 1 mm to 10 mm when inflated and the thickness of the porous material is about 0.025 mm to 0.250 mm. In an implementation with six (6) needles 96, the probe 94 would produce a lesion that is about 2 cm to 3 cm deep and about 2 cm to 3 cm in diameter.

The exemplary tissue penetrating needles 96 each include infusion and ventilation sub-lumens 108 and 110 with distal ends that respectively terminate at infusion and ventilation apertures 112 and 114 within the therapeutic element 104. The proximal ends of the infusion and ventilation sub-lumens 108 and 110 in each of the needles 96 are connected to the infusion lumen 56 and ventilation lumen 58 by a pair of suitable plumbing junctions located within the handle 16".

It should be noted that, because the needles 96 are moved back and forth relative to the 12, the conductors 38 and 40 and sub-lumens 108 and 110 should include some slack within the handle 16".

In addition to conducting energy, the conductive fluid may be continuously infused and ventilated through the therapeutic elements 104 such that it draws heat away from the therapeutic element and the tissue adjacent thereto. This results in the formation of relatively deep, large volume lesions (as compared to devices with conventional needle electrodes) without charring and coagulation. Cooling the therapeutic elements 104 and the adjacent tissue also greatly reduces the amount of time required to form a large volume lesion (as compared to devices with conventional needle electrodes) because higher power is provided when heat is removed from the area adjacent to the needles 96.

Each of the devices described above may be operated in both low voltage modes and high voltage modes. In an exemplary low voltage mode, RF energy will be applied that has a waveform shape and duration that electrically heats and kills tissue in the target region. A typical lesion within the heart could formed by delivering approximately 150 watts of power for about 10 to 120 seconds at a radio frequency of 500 kHz. Applied voltages may range from 60 to 100 volts rms.

Turning to high voltage modes, high voltage energy pulses can be used to kill, coagulate or otherwise modify tissue in at least three ways. For example, the creation of high voltage gradients within the tissue dielectrically breaks down tissue structures. In addition, ohmically heating tissue will coagulate tissue structures, while ohmically heating to very high temperatures will vaporize tissue.

With respect to killing tissue through the dielectric breakdown of cell membranes, relatively short (about 0.1 msec) high voltage (about 400 to 4000 volts with 1000 volts being preferred) RF pulses that result in voltage gradients at or above 500 volts/cm being induced in tissue will accomplish the desired result. Turning to heating, a high voltage RF pulse (about 500 to 1200 volts in magnitude and about 50 to 100 msec in duration) delivers relatively high power to tissue, thereby enabling very rapid heating. Because the tissue is heated rapidly, there is essentially no convective heat loss during power application. Tissue vaporization can be performed through the use of high voltage energy pulses with a pulse duration of about 250 msec to 1 sec. Additional information concerning high and low voltage tissue modification is provided in U.S. Pat. No. 6,023,638, which is incorporated herein by reference.

Although the present inventions have been described in terms of the preferred embodiments above, numerous modifications and/or additions to the above-described preferred embodiments would be readily apparent to one skilled in the art. It is intended that the scope of the present inventions extend to all such modifications and/or additions and that the scope of the present inventions is limited solely by the claims set forth below.

We claim:

1. A surgical probe, comprising:
   a relatively short shaft defining a distal portion, a distal end and a proximal portion;
   a handle attached to the proximal portion of the shaft;
   a plurality of tissue penetrating needles defining distal portions slidably mounted within the shaft and movable relative to the shaft such that the distal portions of the needles extend outwardly from the distal end of the shaft, the plurality of tissue penetrating needles each having a main body, a sharpened distal tip, and at least one lumen; and
   a plurality of inflatable therapeutic elements respectively mounted on the plurality of needles, wherein a distal end of the at least one lumen is disposed within the inflatable therapeutic element and a proximal portion of the at least one lumen is disposed with the handle, wherein the proximal portion of each lumen includes slack disposed within the handle.

2. A surgical probe as claimed in claim 1, wherein the relatively short shaft is relatively stiff.

3. A surgical probe as claimed in claim 1, wherein the relatively short shaft is malleable.

4. A surgical probe as claimed in claim 3, wherein the proximal portion of the relatively short shaft is stiffer than the distal portion of the relatively short shaft.

5. A surgical probe as claimed in claim 1, wherein at least a portion of each of the inflatable therapeutic elements comprises micropores.

6. A surgical probe as claimed in claim 1, wherein the distal portions of the needles define a preset curvature.

7. A surgical probe as claimed in claim 1, wherein at least a portion of each of the inflatable therapeutic elements comprises pores that are less than or equal to 0.1 mm in diameter.

8. A surgical probe system, comprising:
   a surgical probe including a handle, a relatively short shaft defining a distal portion, a distal end and a proximal portion, a plurality of tissue penetrating needles each having a main body and a sharpened distal tip, the proximal portion of the shaft being attached to the handle, the plurality of tissue penetrating needles defining distal portions slidably mounted within the shaft and movable relative to the shaft such that the distal portions of the needles extend outwardly from the distal end of the shaft, a plurality of inflatable therapeutic elements respectively mounted on the plurality of needles, wherein each needle includes at least one lumen having a distal end disposed within the inflatable therapeutic element and a proximal portion disposed with the handle, wherein the proximal portion of each lumen includes slack disposed within the handle; and
   a fluid source operably connected to the plurality of inflatable therapeutic elements and adapted to maintain pressure within the plurality of inflatable therapeutic elements at a predetermined level.

9. A surgical probe system as claimed in claim 8, wherein the relatively short shaft is malleable.

10. A surgical probe system as claimed in claim 8, wherein at least a portion of each of the inflatable therapeutic elements comprises micropores.

11. A surgical probe system as claimed in claim 8, wherein the fluid source comprises a pump.

12. A surgical probe system as claimed in claim 8, wherein
   the at least one lumen includes an infusion lumen and a ventilation lumen that are in fluid communication with the inflatable therapeutic elements;
   the fluid source includes an inlet connected to the surgical probe ventilation lumen and an outlet connected to the surgical probe infusion lumen; and
   the fluid source continuously infuses fluid to and ventilates fluid from the inflatable therapeutic elements by way of the outlet and inlet.

13. A surgical probe system as claimed in claim 8, wherein the distal portions of the needles define a preset curvature.

14. A surgical probe system as claimed in claim 8, wherein at least a portion of each of the inflatable therapeutic elements comprises pores that are less than or equal to 0.1 mm in diameter.

15. A surgical probe system, comprising:
   a surgical probe including a handle, a relatively short shaft defining a distal portion, a distal end and a proximal portion, a plurality of tissue penetrating needles each having a main body, a sharpened distal tip, and at least one lumen, the proximal portion of the shaft being attached to the handle, the plurality of tissue penetrating needles defining distal portions slidably mounted within the shaft and movable relative to the shaft such that the distal portions of the needles extend outwardly from the distal end of the shaft, and a plurality of inflatable therapeutic elements respectively mounted on the plurality of needles, wherein a distal end of the at least one lumen is disposed within the inflatable therapeutic element and a proximal portion of the at least one lumen is disposed with the handle, wherein the proximal portion of each lumen includes slack disposed within the handle; and means, operably connected to the plurality of inflatable therapeutic elements, for inflating the plurality of inflatable therapeutic elements with electrically conductive fluid and maintaining pressure within the plurality of inflatable therapeutic elements at a predetermined level.

16. A surgical probe system as claimed in claim 15, wherein the relatively short shaft is malleable.

17. A surgical probe system as claimed in claim 15, wherein at least a portion of each of the inflatable therapeutic elements comprises micropores.

18. A surgical probe system as claimed in claim 15, wherein at least a portion of each of the inflatable therapeutic elements comprises pores that are less than or equal to 0.1 mm in diameter.

19. A surgical probe system as claimed in claim 15, wherein the distal portions of the needles define a preset curvature.

\* \* \* \* \*

UNITED STATES PATENT AND TRADEMARK OFFICE
CERTIFICATE OF CORRECTION

| | | |
|---|---|---|
| PATENT NO. | : 8,795,271 B2 | Page 1 of 1 |
| APPLICATION NO. | : 12/175433 | |
| DATED | : August 5, 2014 | |
| INVENTOR(S) | : Koblish et al. | |

It is certified that error appears in the above-identified patent and that said Letters Patent is hereby corrected as shown below:

In the Specification

Column 8
Line 18: after "exceed 90° C", delete "."
Line 60: after "temperature above 100° C", delete "."

Column 11
Line 65: after "be heated to about 90° C", delete "."

Signed and Sealed this
Fourteenth Day of October, 2014

Michelle K. Lee
*Deputy Director of the United States Patent and Trademark Office*